United States Patent [19]

Harisiades

[11] Patent Number: 4,962,178

[45] Date of Patent: Oct. 9, 1990

[54] POLYSILOXANE-POLYURETHANES AND CONTACT LENS THEREOF

[75] Inventor: Paul Harisiades, Woodhaven, N.Y.

[73] Assignee: Ciba-Geigy Corporation, Ardsley, N.Y.

[21] Appl. No.: 266,555

[22] Filed: Nov. 3, 1988

[51] Int. Cl.$^5$ .................. C08G 77/20; C08G 77/388
[52] U.S. Cl. ............................. 528/33; 528/28; 525/453; 525/474; 525/477
[58] Field of Search .............. 528/28, 33; 525/453, 525/474, 477

[56] References Cited

U.S. PATENT DOCUMENTS

| | | | |
|---|---|---|---|
| 3,179,622 | 4/1965 | Haluska | 528/31 |
| 3,562,352 | 2/1971 | Nyilas | 525/453 |
| 4,202,807 | 5/1980 | Moretto et al. | 524/263 |
| 4,292,423 | 9/1981 | Kaufmann et al. | 528/18 |
| 4,590,224 | 5/1986 | Frisch | 521/155 |
| 4,644,046 | 2/1987 | Yamada | 528/28 |
| 4,692,476 | 9/1987 | Simpson | 521/112 |
| 4,740,533 | 4/1988 | Su et al. | 523/106 |

FOREIGN PATENT DOCUMENTS 63083121 4/1982 Japan .
57-156005 9/1982 Japan .

OTHER PUBLICATIONS

V. V. Astakhin et al., J. General Chem. (USSR), 29, 887 (1959).
K. A. Andranor et al., J. General Chem (USSR), 29, 2665 (1959).
Noll, Chemistry & Technology of Silicones, Academic Press, 1968 pp. 94–101.
Chem. Abst. 52, 9652a.
Chem. Abst. 30, 6670b (1959).
Chem. Abst. 33, 15153h (1962).
V. V. Astakhin et al., Doklady Akad. Nauk, S.S.S.R. 113, 581 (1957)(=C.A. 51, 14582i (1957)).
V. V. Astakhin et al., Zhur Obshchei Khim, 29, 904 (1959) (=C.A. 54, 1371f (1959)).

Primary Examiner—Melvyn I. Marquis
Assistant Examiner—R. Dean, Jr.
Attorney, Agent, or Firm—Luther A. R. Hall

[57] ABSTRACT

A novel polysiloxane polyurethane is described which is obtained by reaction of an isocyanate capped polysiloxane prepolymer with a polysiloxane-disilanol and which contains O-silyl-urethane linkages. The novel polysiloxane-polyurethanes are useful as oxygen permeable membranes or films, as bandages and drug carriers, for example in transdermal drug delivery, and especially as highly oxygen permeable, soft contact lenses.

10 Claims, No Drawings

POLYSILOXANE-POLYURETHANES AND CONTACT LENS THEREOF

BACKGROUND OF THE INVENTION

Silicones occupy an important place in the chemical industry in a variety of applications ranging from lubricants to sealants. Silicone fluids composed of polydimethylsiloxane combine many useful properties such as excellent thermal stability, chemical inertness, small changes in viscosity with changes in temperature, high oxygen permeability, outstanding shear stability, and excellent lubricity. They have found extensive use as adhesives, sealants, coatings, softeners, lubricants, dispersants, and antifoam agents in non-aqueous systems in industries as diverse as construction, pharmaceuticals, rubber, plastics, textiles, cosmetics, printing and founding.

More recently silicone rubber materials have been used in biomedical products such as artificial organs and contact lenses. The great benefit of silicone to the latter stems from its high permeability to oxygen although this advantage is offset by its intrinsic hydrophobicity. For this reason all present commercial contact lens formulations which incorporate silicone are hard lens formulations which contain it only in limited amounts. It would be highly desirable to produce a contact lens composed entirely of silicone rubber since it offers the highest oxygen permeability of all presently available materials. The enhancement of eye comfort and wearing time would represent a significant improvement in contact lens technology. However, this goal cannot be achieved until the hydrophobic surface of the silicone is rendered hydrophilic by some kind of surface modification, since silicone rubber alone adheres very strongly to the cornea and also rapidly attracts particulate matter.

Silicone rubber is made by crosslinking liquid polysiloxanes. These rubbers are thermoset polymers which can be made to varying degrees of hardness and elasticity by controlling the degree of crosslinking and the molecular weight of the silicone fluid. Silicone rubber is usually made by vulcanizing polydimethylsiloxane fluids with organic peroxides at elevated temperatures. Another approach to crosslinking employs hydrosilation in which poly(vinylalkylsiloxanes) are cured with poly(hydridoalkylsiloxanes) in the presence of transition metal catalysts. Silicone rubber has also been formed by chemically reacting, α,ω-difunctional poly(-diorganosiloxanes) with polyfunctional silanes and siloxanes. Typically the crosslinking reaction is a condensation which forms a siloxane bond and a volatile by product. Common examples of this type of cure reaction are silanolalkoxylsilane (French Pat. No. 1,042,019), silanol-acetoxysilane (L. F. Ceyzeriat and P. Dumonth, German Appl. No. 1,121,803), silanol-silane (Midland Silicones, Brit. Pat. No. 804,199), and silanol-silanol (via the corresponding acetone oxime) (E. Sweet, Dow Corning, Belg. Pat. No. 614,394. Suitable catalysts for these reactions are amines and carboxylic acid salts of Sn, Pb, Zn, Sb, Fe, Cd, Ba, Ca and Mn.

Organosiloxane isocyanates have been prepared (U.S. Pat. No. 3,179,622) which vulcanize when exposed to moisture. In these cases the isocyanate group is joined to the siloxane through an alkyl group, rendering it unhydrolyzable.

Relatively few reports exist for the curing of silicones via the reaction of a silanol with an isocyanate yielding an θ-silylurethane linkage. This is probably due to the well known hydrolytic instability of this bond. To our knowledge there are no existing reports of a silicone rubber crosslinked by O-silylurethane bonds that is resistant to hydrolytic decomposition.

The use of silanol terminated polydimethylsiloxanes has been reported in the modification of polysiloxanes with polyurethanes (Moretto, U.S. Pat. No. 4,202,807) to improve the mechanical properties of the former at elevated temperatures. No mention was made of the hydrolytic stability of the O-silylurethane bond in these materials. The only other mention of this bond in a polymeric material was made by Kaufman, Muller, and Wegchaupt (U.S. Pat. No. 4,292,423 in the preparation of organopolysiloxanes for coating purposes. However, when the claimed organopolysiloxane was prepared entirely through the reaction of siloxane groups with isocyanate groups (Example 1 of this patent), the coating was decomposed by atmospheric moisture and addition of 75% by weight of the polyurethane, Desmodur L, was necessary to produce a hydrolytically stable coating.

High hydrolytic susceptibility is a property characteristic of O-silylurethanes since they were first reported by Andrianov, Losev, and Astakhin (Proc. Akad. Sci., USSR, Sect. Chem 113, 247, [1957]) from the reaction of triethylsilanol and m-toluene-diisocyanate. These authors subsequently described their alcoholysis and hydrolysis (J. General Chem., USSR, 29,2665, [1959]). This behavior of O-silylurethanes has been summarized by Noll in "Chemistry and Technology of Silicones," Academic Press, 1968, pp 99–100.

It has now unexpectedly been discovered, that by reaction of essentially equivalent amounts of diisocyanate-capped poly-dialkylsiloxanepolyalkanols and poly-dimethylsiloxane-disilanols, a clear, flexible and elastic siloxane polyurethane rubber is obtained which is completely resistant to hydrolysis under physiological conditions, despite the fact that half of all urethane groups in the polymer contain the —Si—O—C— bond. This novel polysiloxane-polyurethane is uniquely suited as a biocompatible, oxygen-permeable membrane or film and especially, as a crosslinked rubber, as a soft contact lens.

It has further been discovered that this polyurethane is uniquely suited to be grafted to polyvinylalcohol or hydroxyalkyl cellulose and thereby allows production of a composite material not only with excellent optical clarity and the characteristically high permeability to oxygen, but also with high wettability as well.

DETAILED DESCRIPTION

The instant invention pertains to a polymer, suitable for use as an oxygen permeable membrane or an ophthalmic device, having based on total urethane groups 50 to 80% of alkyl-urethane —C—NH—COO—C— groups and 50 to 20% of silyl-urethane —C—NH—COO—Si— groups, which comprises the polymerization product of (a) 80–95% by weight (based on the total polymer) of a poly-isocyanate capped, linear or branched polysiloxane prepolymer, having a molecular weight of about 1000 to about 10,000 and containing at least one isocyanate group per 3000 molecular weight unit of polysiloxane, said isocyanate groups being attached to the polysiloxane through urethane linkages, said polysiloxane prepolymer having the structure $A_1$, $A_2$, $A_3$ (which are described in detail below); and (b) 20-5% by weight (based on the total polymer) of a linear polydialkyl- or polydiphenyl-siloxane disilanol (B)

$$\text{HO} - \left[ \begin{array}{c} E_a \\ | \\ \text{SiO} \\ | \\ E_b \end{array} \right]_n - \text{H} \qquad (B)$$

having a molecular weight from about 240 to about 1000 and containing terminal silanol groups, where n is 2-50, and $E_a$ and $E_b$ are alkyl of 1 to 4 carbon atoms or phenyl.

Prepolymer A:

The linear or branched polysiloxane prepolymer A is of one of the following general structures, $A_1$, $A_2$, or $A_3$:

$$X-R_1-\left[\begin{array}{c}R_a\\|\\ \text{SiO}\\|\\ R_g\end{array}\right]_{x_1}-\left[\begin{array}{c}\left[\begin{array}{c}R_b\\|\\ \text{SiO}\\|\\ R_1\\|\\ X\end{array}\right]\left[\begin{array}{c}R_c\\|\\ \text{SiO}\\|\\ R_f\end{array}\right]_{x_2}\end{array}\right]_{y_1}\begin{array}{c}R_d\\|\\ \text{Si}-R_1-X_1\\|\\ R_f\end{array} \qquad (A_1)$$

$$(R_2)_3\text{SiO}-\left[\begin{array}{c}R_g\\|\\ \text{SiO}\\|\\ R_k\end{array}\right]_{x_1}-\left[\begin{array}{c}\left[\begin{array}{c}R_h\\|\\ \text{SiO}\\|\\ R_1\\|\\ X\end{array}\right]\left[\begin{array}{c}R_i\\|\\ \text{SiO}\\|\\ R_j\end{array}\right]_{x_2}\end{array}\right]_{y_2}-\text{Si}(R_2)_3 \qquad (A_2)$$

$$X-\text{CH}_2-\overset{X}{\underset{|}{\text{CH}}}\text{CH}_2\text{O}(\text{CH}_2)_3-\left[\begin{array}{c}R_a\\|\\ \text{SiO}\\|\\ R_c\end{array}\right]_n-\begin{array}{c}R_b\\|\\ \text{Si}-(\text{CH}_2)_3-\text{OCH}_2-\overset{X}{\underset{|}{\text{CH}}}\text{CH}_2-X_3\\|\\ R_d\end{array} \qquad (A_3)$$

wherein:
$R_1$ is a linear or branched alkylene group with 2-6 carbon atoms or a polyoxyalkylene group of structures $$-[\text{CH}_2\text{CHO}]_p\text{CH}_2\text{CH}- \quad \text{or} \quad -(\text{CH}_2)_3\text{OCH}_2\text{CHCH}_2- $$
$$\qquad\quad\; \underset{R_3}{|} \qquad\quad\; \underset{R_3}{|} \qquad\qquad\qquad\quad \underset{\text{OCH}_3}{|}$$

wherein $R_3$ is hydrogen or methyl and p is an integer from 1-50, $R_2$, $R_a$, $R_b$, $R_c$, $R_d$, $R_e$, $R_f$, $R_g$, $R_h$, $R_i$, $R_j$, $R_k$ are independently methyl or phenyl; $x_1$, $x_2$ are integers from 1 to 500 with the proviso that the sum of $x_1+x_2$ is 12 to 1,000, $y_1$ is 0 to 4 and $y_2$ is 2 to 5 with the proviso that the respective ratios of $$\frac{x_1 + x_2 y_1}{y_1 + 2} \text{ (for } A_1\text{)} \quad \text{and} \quad \frac{x_1 + x_2 y_2}{y_2} \text{ (for } A_2\text{)}$$

are not greater than 70.

$$X = -\underset{\underset{O}{\|}}{\text{OC}}-\underset{|}{\overset{H}{\text{N}}}-R_4-\text{NCO}$$

$$X_1 \text{ is X or } -\underset{\underset{O}{\|}}{\text{OCN}}-\overset{H}{\underset{|}{}}R_4-\overset{H}{\underset{|}{\text{N}}}\underset{\underset{O}{\|}}{\text{CO}}-T_1 \text{ and}$$

$$X_3 \text{ is X or } -\underset{\underset{O}{\|}}{\text{OCN}}-\overset{H}{\underset{|}{}}R_4-\overset{H}{\underset{|}{\text{N}}}-\underset{\underset{O}{\|}}{\text{CO}}-T_3$$

wherein
$R_4$ is a di-radical obtained by removing the NCO-groups from an aliphatic, cycloaliphatic or aromatic di-isocyanate;

A preferred embodiment of the instant invention is a polymer where component A is a polysiloxane of structure $A_1$ or $A_2$, $R_1$ is alkylene or 3 or 4 carbon atoms, $R_2$, $R_a$, $R_b$, $R_c$, $R_d$, $R_e$, $R_f$, $R_g$, $R_h$, $R_i$, $R_j$, $R_k$ are each methyl, $x_1+x_2$ is 12 to 100, $y_1$ is 0 to 2, $y_2$ is 2 to 3, and $R_4$ is a diradical of an aliphatic or cycloaliphatic diisocyanate with 6 to 10 carbon atoms.

A most preferred embodiment of the instant invention is a polymer where component A is a polysiloxane of structure $A_1$.

Poly-functional polysiloxanes, useful as starting materials for the prepolymer (A), are of structures:

$$\text{HOR}_1-\left[\begin{array}{c}R_a\\|\\ \text{SiO}\\|\\ R_g\end{array}\right]_{x_1}-\left[\begin{array}{c}\left[\begin{array}{c}R_b\\|\\ \text{SiO}\\|\\ R_1\\|\\ \text{OH}\end{array}\right]\left[\begin{array}{c}R_c\\|\\ \text{SiO}\\|\\ R_f\end{array}\right]_{x_2}\end{array}\right]_{y_1}\begin{array}{c}R_d\\|\\ \text{Si}-R_1-\text{OH}\\|\\ R_f\end{array} \qquad (A_1')$$

$$(R_2)_3\text{SiO}-\left[\begin{array}{c}R_g\\|\\ \text{SiO}\\|\\ R_k\end{array}\right]_{x_1}-\left[\begin{array}{c}\left[\begin{array}{c}R_b\\|\\ \text{SiO}\\|\\ R_1\\|\\ \text{OH}\end{array}\right]\left[\begin{array}{c}R_h\\|\\ \text{SiO}\\|\\ R_j\end{array}\right]_{x_2}\end{array}\right]_{y_2}-\text{Si}(R_2)_3 \qquad (A_2')$$

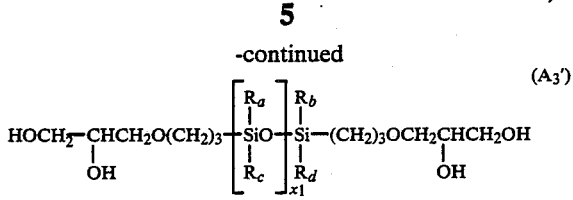

wherein:

$R_1$, $R_a$, $R_b$, $R_c$, $R_d$, $R_e$, $R_f$, $R_g$, $R_h$, $R_i$, $R_j$, $R_k$, $x_1$, $x_2$, $y_1$, $y_2$ are described above.

Di- and tri-isocyanates useful to form the prepolymer intermediate are aliphatic, cycloaliphatic or aromatic polyisocyanates and include: ethylene diisocyanate, 1,2-diisocyanatopropane, 1,3-diisocyanatopropane, 1,6-diisocyanatohexane, 1,6-diisocyanato-2,2-4-(2,4,4)-trimethylhexane, 2,2′-diisocyanatodiethyl fumarate, 1,2-, 1,3-, 1,5-, 1,6-, 1,7-, 1,8-, 2,7- and 2,3-diisocyanatonaphthalene; 2,4- and 2,7-diisocyanato-1-methylnaphthalene; 1,4-diisocyanatobiphenyl; 1,2-diisocyanatocylohexane, 1,3-diisocyanatocyclo-hexane, 1,4-diisocyanatobenzene, bis(4-isocyanatocyclohexanyl)methane, bis(4-isocyanato-phenyl)methane, 1,2 and 1,4-toluene diisocyanate, 3,3-dichloro-4,4′-diisocyanatobiphenyl, tris-(4-isocyanatophenyl)methane, hydrogenated toluene diisocyanate, 1-isocyanatomethyl-5-isocyanato-1,3-3-trimethylcyclohexane (=isophorone diisocyanate).

The diisocyanates can be used alone or in combination with each other.

Preferred are aliphatic diisocyanates, with isophorone-diisocyanate and 1,6-diisocyanato-2,2,4-(-2,4,4)trimethylhexane being most preferred.

Disilanol Component B:

The linear polydialkyl- or polyphenyl-siloxane disilanol is of structure (B)

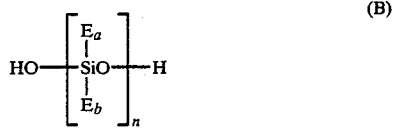

where $n=2-50$, and $E_a$ and $E_b$ are alkyl of 1 to 4 carbon atoms, or phenyl; preferably methyl.

Preferred are polydimethylsiloxane-disilanols within=3-6 and $E_a$, $E_b$ and methyl.

Preferably the polymers of the instant invention are useful as ophthalmic devices such as contact lenses or intraocular lenses. Most preferably the polymers are useful as contact lenses.

SYNTHESIS

The isocyanato functional polysiloxane prepolymers $A_1$-$A_3$ are obtained conveniently from the corresponding poly-hydroxyalkylene functional polysiloxanes by the known techniques of polyurethane prepolymer synthesis. Polysiloxane di-, tri- and tetraalkanols can be used alone or as mixtures, as long as the functionality of the mixture is greater than 2. As a first step, the polysiloxane is reacted, either in bulk or in solution, with a given amount of di- or triisocyanate, preferably in the presence of a catalyst. This catalyst may be a tertiary amino group containing compound such as triethylamine, pyridine or diaminobicyclooctane, or a metal based catalyst like dibutyltin dilaurate or stannous octoate. The reaction is carried out at either ambient or elevated temperatures under a dry nitrogen blanket and can be followed conveniently by NCO-titration or IR analysis.

The molar ratio of OH to NCO groups can be 1:1.5 to 1:3 and is preferably in the range of 1:2.05–1:2.1.

Although it is preferable to react one equivalent reactive polysiloxane with close to two equivalents diisocyanate and thereby obtain an isocyanate-endcapped polysiloxane, due to the laws of polycondensation kinetics a certain amount of chain extended product, in which the endcapped polymer contains two polysiloxane chains connected by a diisocyanate unit, is always obtained and can be analyzed, for instance by gel permeation chromatography.

It is therefore within the scope of the present invention to use as polysiloxanes prepolymer obtained from polysiloxanes of structures $A_1$ and $A_3$ by chain-extension reactions commonly used by those skilled in the art of polycondensation, especially polyurethane chemistry. Such chain extensions can be achieved by instance by polycondensation of the aforementioned polysiloxane diols, with: diacid chlorides or anhydrides or dianhydrides, such as teraphthaloyl chloride, adipic acid dichloride, maleic anhydride, phthalic anhydride or benzophenone-tetracarboxylic acid and dianhydride, but preferably with diisocyanates of the structures mentioned above, in which case the synthesis step for preparing the NCO-capped prepolymer as described is simply carried out with less than a 2:1 excess of NCO over —OH—groups, likewise, the NCO-terminated prepolymers obtained before the final capping step is carried out with the hydroxy-vinyl compounds, can be chain extended with diols or diamines according to the known techniques of polyurethane technology, with for example, ethylene glycol, propylene glycol, bulanediol, hexanediol or polyetherdiols containing ethyleneoxide, propylene oxide or n-butylene oxide repeating units or fluorinated polyether groups; polyester diols ethylenediamine, hexanediamine and diprimary or di-secondary amines in general, including diamines derived from polyalkylene oxides. To the extent that through these chain extension reactions additional amide, urethane or urea groups are introduced into the structure, they contribute by hydrogen-bonding to the rigidity and clarity of the polymer. Chain extensions of the sort just described, however, dilute the overall polysiloxane extent of the polymer and therefore lower the oxygen permeability in the final polymer.

For producing contact lenses, the thoroughly mixed components—isocyanate capped polysiloxane prepolymer, polysiloxane-disilanol and catalyst—are filled into one part of the contact lens mold, the mold is closed and the assembly is kept at the reaction temperature (50°–80°) for the required length of time, after which the mold is opened up and the lens is taken out.

Since polysiloxane-rubbers, including the one described in this invention, are very hydrophobic and therefore by themselves unsuited as contact lens materials, the surfaces of the prepared lenses need to be made hydrophilic. This can be achieved by surface treatments or preferably by transfer grafting polyvinyl alcohol (PVA) or hydroxy-ethyl cellulose (HEC), as described in a copending patent application Ser. No. 250,199. For transfer-grafting, the contact lens molds are coated with a thin (0.5–10 micron) film of PVA or HEC prior to casting the lens. During polymerization, the PVA or HEC film is transferred from the mold to the forming polymer by covalent bonding via urethane linkages. After the lens is removed, an extremely wettable surface is obtained, which is not dissolved away in hot water or in a solvent and resists abrasion. It has been discovered that the polysiloxane-polyurethanes of this invention are uniquely suited for carrying out the transfer-grafting process described in copending patent application Ser. No. 250,199 by using polyvinyl alcohol as surface coating. Thus, contact lenses prepared according to this invention in a mold coated with PVA or hydroxyalkyl cellulose area preferred embodiment of this invention.

The following examples are presented for the purpose of illustration only and are not to be construed to limit the nature and scope of the invention in any manner whatsoever.

The following examples, specific oxygen permeability ($O_2.DK$) is determined by measuring dissolved oxygen permeability at 25° C. with a polarographic electrode in an air-saturated aqueous environment and is expressed in units $$O_2.DK = \frac{cm^3(STP)x \cdot cm}{cm^2 \times sec \times cmHg} \times 10^{10} \text{ (barrers)}$$

Wettability is determined by measuring the contact angle of an n-octane droplet which had risen to the lower surface of a 1 mm thick sample sheet immersed in octane saturated distilled water at 36° C.

Tensile strength, Young's modulus and elongation where measured on 1 mm thick sheets using an INSTRON model 1123 testing apparatus.

Hardness is determined using a Shore-A durometer on center cut buttons of 10 mm diameter and 8 mm height.

EXAMPLE 1

(a) Synthesis of Tri-isocyanate Macromer:

Polydimethylsiloxane trialkanol of structure $A_2$ (MW:; 6690) (159.86 g, 0.0277 mole) are mechanically stirred with two equivalents of isophorone diisocyanate (IPDI), (18.56 g, 0.0832 mole) under a nitrogen atmosphere. After ten minutes, dibutyltin dilaurate (DBTL) (32 mg, 0.02%) catalyst is added. The reaction mixture becomes homogeneous 90–120 minutes after addition of the catalyst and the NCO concentration reaches the theoretical level after six hours and does not change with further stirring. The triisocyanate macromer is stored at 5° C under nitrogen in plastic containers. It has an intrinsic viscosity $[\eta]$ of 0.13 and a MW, based on % NCO, of 7400. Its dispersity, by GPC, is 5.9.

(b) Preparation of oligomeric siloxane diols from $\alpha,\omega$-siloxane dichloride The siloxane diols are prepared by hydrolysis of the corresponding siloxane dichlorides in a cooled mixture of pH 7 buffered water and diethyl ether. After extraction, the polysiloxane diols are purified by distillation. The following disilanols

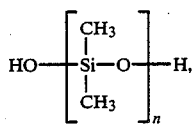

are prepared:

| | MW | YIELD | bp(°C.) |
|---|---|---|---|
| n = 3 | 240 | 87 | 72–74° C. 0.3 mm |

-continued

| | MW | YIELD | bp(°C.) |
|---|---|---|---|
| 4 | 314 | 85 | 86–88° C. 0.4 mm |
| 6 | 463 | 86 | 113° C. 1.2 mm |
| 8 | 611 | 82 | 135° C. 0.4 mm |

These oligomers are stable with respect to self-condensation when stored in plastic containers under nitrogen.

(c) Preparation of O-Silylurethane Crosslinked Silicone Rubber

The polydimethylsiloxane tri-isocyanate macromer (M 7400) (24.25 g, 3.286 m mole) is stirred in vacuo (15 torr) with hexamethyltrisiloxane diol (1.14 g, 4.765 m mole) for 30 minutes. The formulation is stable for over 30 days when stored under nitrogen at 5° C., at room temperature the formulation is stable for one week. Five square inch sheet molds are filled with the siloxane formulations in thickness of 1.0 mm, 0.5 mm, 0.3 mm and 0.1 mm. The molds are made against MYLAR, which has previously been coated with a thin layer (1.0μ) of PVA ($M_n$ 41,000, $M_w$ 114,000) which becomes grafted to the silicone during cure, leaving it with a clear, wettable surface. Polypropylene button molds (diam.=15 mm, height=10 mm) are also filled. Curing is done at 60° C. under a nitrogen atmosphere for 24 hours. A clear, resilient rubber is obtained which is completely resistant to hydrolysis in distilled water at 80° C. for one month. Hardness measurements, as well as degree of swelling and percent extractibles after two weeks in absolute ethanol are made on buttons weighing approximately 2.3 g.

EXAMPLE 2

The polydimethylsiloxane tri-isocyanate macromer of Example 1 (M 7400) (22.47 g 3.047 m moles) is mixed with octamethyltetrasiloxane diol (1.38 g, 4.419 m mole) on a rotoevaporator in vacuo (15 torr) for 30 minutes. Polymers are cast in form of sheets and buttons, as described in Example 1-c, with curing carried out at 60° C. in a nitrogen atmosphere for 24 hours.

| | Initial | After 4 weeks at 80° C. in distilled water |
|---|---|---|
| Tensile strength [kg/cm$^2$] | 7.27 | 7.32 |
| Young's modulus [kg/cm$^2$] | 10.67 | 10.73 |
| Elongation to break (%) | 150 | 180 |
| Shore A hardness | 34 | — |
| Contact Angles | | |
| Advancing | 32 | 35 |
| Receding | 27 | 24 |
| Ethanol swelling (%) | 39.2 | — |
| Extractibles (%) | 1.2 | — |
| $O_2.DK$ (barrers) | 376 | |

EXAMPLE 3

(a) Synthesis of Tri-isocyanate Macromer

Polydimethylsiloxane trialkanol of Structure $A_1$ (MW 6280), (270.14 g, 43.00 m mole) is mechanically stirred with two equivalents of isophorone diisocyanate (IPDI) (29.65 g, 133.40 m moles) under a nitrogen atmosphere. The temperature is raised to 50° C. for 3 hours after which time the NCO level drops to the theoretical level. The triisocyanate macromer is stored at 5° C. under nitrogen in plastic containers. It has a molecular weight, based on % NCO, of 6980, and a polydispersity, by GPC of 20.6.

(b) Preparation of Silyl-Urethane Crosslinked Silicone Rubber

The polydimethyl siloxane tri-isocyanate macromer (MW 6980) (20.91 g, 3.00 m mole) is stirred in vacuo (15 torr) with hexamethyltrisiloxane diol (1.08 g, 4.50 m mole) for 30 minutes. The formulation is stable for over 30 days when stored under nitrogen at 5° C., at room temperature the formulation is stable for 48 hours. Five inch square sheet molds are filled with the siloxane formulations in thickness of 1.0 mm, 0.5 mm, 0.3 mm and 0.1 mm. The molds are made against MYLAR, which has previously been coated with polyvinyl alcohol, as described in Example 1. Polypropylene button molds (diam.=15 mm, height=10 mm) are also filled and curing is done at 60° C. under a nitrogen atmosphere for 24 hours. A clear, resilient rubber is obtained which is completely resistant to hydrolysis in distilled water at 80° C. for one month.

EXAMPLE 4

Example Using Structure A$_3$ (Mercor Tetraol (a) Synthesis of Tetra-isocyanate Macromer Polydimethylsiloxane tetra-alkanol of structure A$_3$ (MW 3400) (167.18 g, 49.17 m mole) is mechanically stirred with two equivalents of isophorone diisocyanate (IPDI) (43.72 g 196.7 m mole) for ten minutes under a nitrogen atmosphere. Then dibutyltin-dilaurate (33 mg, 0.02%) catalyst is added. The theoretical endpoint is reached after 21 hours of stirring. The tetra-isocyanate macromer is stored at 5° C. under nitrogen in plastic containers and has a MW of 4265 (by NCO titration).

(b) Preparation of a Silyl Urethane Crosslinked Silicone Rubber

The polydimethylsiloxane tetra-isocyanate macromer (MW 4265) (16.79 g, 3.94 m mole) is stirred on a rotoevaporator in vacuo (25 torr) with octamethyltetrasiloxane diol (2.47 g, 7.88 m mole) for 30 minutes. The mixture is filled into molds and cured at 60° C. under a nitrogen atmosphere for 24 hours as described in Example 1. A clear, resilient rubber is obtained which is completely resistant to hydrolysis in distilled water for 80° C. for one month.

EXAMPLE 5

Preparation of a Contact Lens

The silicone composition described in Example 1c is prepared. Zero expansion poly(propylene) lens molds are dip coated with a 2% solution of EPVA in water-isopropanol (4:1) containing 0.1% LODYNE S-100 surfactant (CIBA-GEIGY). After drying in a 60° C. oven for one hour, each mold is filled with four drops of the silicone composition and subsequently clamped shut. Curing is carried out as previously described at 60° C. for 24 hours. Lenses are removed by opening the molds and dropping them in boiling water. Clear, resilient, highly wettable lenses are obtained.

What is claimed is:

1. A siloxane-urethane polymer, suitable for use as an oxygen permeable membrane or an ophthalmic device, having based on total urethane groups 50 to 80% of —C—NH—COO—C— groups and 50 and 20% of —C—NH—COO—Si— groups, which consists essentially of the polymerization product of
   (a) 80-95% weight (based on the total polymer) of a poly-isocyanate capped, linear or branched polysiloxane prepolymer, having a molecular weight of about 1000 to about 10,000 and containing at least one isocyanate group per 3000 molecular weight unit of polysiloxane, said isocyanate groups being attached to the polysiloxane through urethane linkages, said polysiloxane prepolymer having the structure A$_1$, A$_2$ and A$_3$

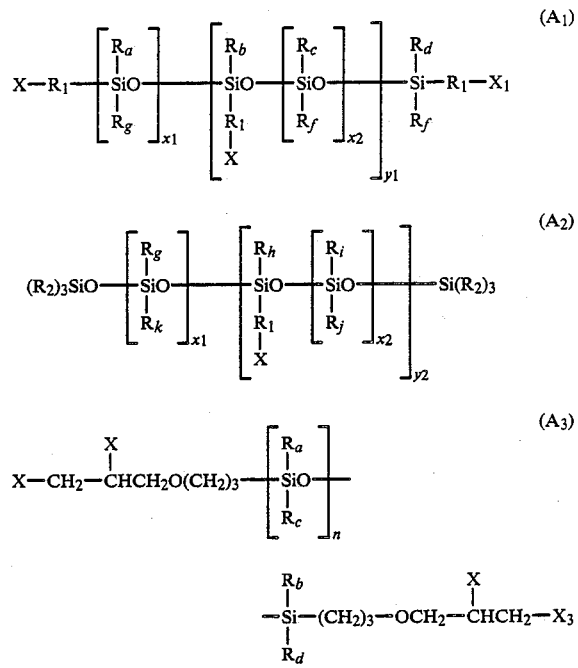

wherein:

R$_1$ is a linear or branched alkylene group with 2–6 carbon atoms or a polyoxyalkylene group of structures

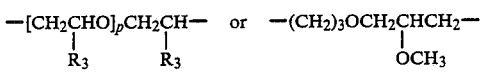

wherein R$_3$ is hydrogen or methyl and p is an integer from 1–50; R$_2$, R$_a$, R$_b$, R$_c$, R$_d$, R$_e$, R$_f$, R$_g$, R$_h$, R$_i$, R$_j$, R$_k$ are independently methyl or phenyl; x$_1$, x$_2$ are integers from 1 to 500 with the proviso that the sum of x$_1$+x$_2$ is 12 to 1,000; y$_1$ is 0 to 4 and y$_2$ is 2 to 5 with the proviso that the respective ratios of $$\frac{x_1 + x_2 y_1}{y_1 + 2} \text{ (for } A_1\text{)} \quad \text{and} \quad \frac{x_1 + x_2 y_2}{y_2} \text{ (for } A_2\text{)}$$

are not greater than 70,

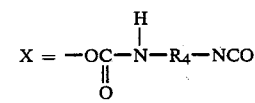

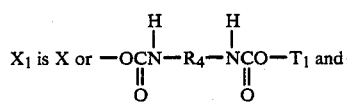

-continued

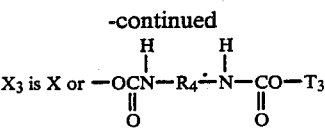

wherein

T₁ is A₁ from which X₁ removed, and

T₃ is A₃ from which X₃ is removed,

R₄ is a di-radical obtained by removing NCO-groups from an aliphatic, cycloaliphatic or aromatic di-isocyanate; and (b) 20-50% by weight (based on the total polymer) of a linear polydialkyl- or polydiphenyl-siloxane disilanol in

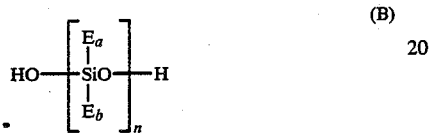

(B)

having a molecular weight from about 240 to about 1000 and containing terminal siloxanol groups, where, n is 2-50 and $E_a$ and $E_b$ are alkyl of 1 to 4 carbon atoms or phenyl.

2. A polymer according to claim 1 which is in the form of an ophthalmic device.

3. A polymer according to claim 2 which is in the form of a contact lens.

4. A polymer according to claim 1 wherein the prepolymer of component (a) has structure $A_1$ or $A_2$.

5. A polymer according to claim 4 wherein the prepolymer of component (a) has structure $A_1$.

6. A polymer according to claim 1 wherein the prepolymer of component (a) has structure $A_1$ or $A_2$, $R_1$ is alkylene of 3 or 4 carbon atoms, $R_2$, $R_a$, $R_b$, $R_c$, $R_d$, $R_f$, $R_g$, $R_h$, $R_i$, $R_j$ and $R_k$ are each methyl, $x_1+x_2$ is 12 to 100, $y_1$ is 0 to 2, $y_2$ is 2 to 3, and $R_4$ is a diradical of an aliphatic or cycloaliphatic diisocyanate with 6 to 10 carbon atoms.

7. A polymer according to claim 1 wherein the prepolymer of component (a) has structure $A_1$, $A_2$ or $A_3$ in which $R_4$ is a diradical obtained by removing the —NCO groups from a diisocyanate selected from the group consisting of ethylene diisocyanate, 1,2-diisocyanatopropane, 1,3-diioscyanatopropane, 1,6-diiso-cyanatohexane, 1,6-diisocyanato-2,2-4-(2,4,4)-trimethylhexane, 2,2'-diisocyanatodiethyl fumarate, 1,2-, 1,3-, 1,5-, 1,6-, 1,7-, 1,8-, 2,7- and 2,3-diisocyanatomaphthalene; 2,4- and 2,7-diisocyanato-1-methylnaphthalene; 1,4-diisocyanatobiphenyl; 1,2-diisocyanatocyclohexane, 1,3-diisocyanatocyclohexane, 1,4-diisocyanatobenzene, bis-(4-isocyanatocyclohexanyl)methane, bis(4-isocyanato-phenyl)methane, 1,2 and 1,4-toluene diisocyanate, 3,3-dichloro-4,4'-diisocyanatobiphenyl, hydrogenated toluene diisocyanate, and isophorone diisocycanate.

8. A polymer according to claim 7 wherein the isocyanate is isophorone diisocyanate or 1,6-diisocyanato-2,2,4-(2,4,4-)-trimethylhexane.

9. A polymer according to claim 1 where in the siloxane disilanol of component (b) $E_a$ and $E_b$ are methyl.

10. A polymer according to claim 9 where in the siloxane silanol of component (b) n is 3-6.

* * * * *